United States Patent [19]

Mohler et al.

[11] Patent Number: 5,589,169
[45] Date of Patent: Dec. 31, 1996

[54] METHOD AND THERAPEUTIC COMPOSITIONS FOR THE PREVENTION OF FIBRIN DEPOSITION OR ADHESIONS

[75] Inventors: Marjorie A. Mohler, Oakland; Tue H. Nguyen, San Mateo, both of Calif.

[73] Assignee: Genentech, Inc., South San Francisco, Calif.

[21] Appl. No.: 511,838

[22] Filed: Apr. 13, 1990

Related U.S. Application Data

[63] Continuation of Ser. No. 125,319, Nov. 25, 1987, abandoned, which is a continuation of Ser. No. 68,872, Jul. 1, 1987, abandoned.

[51] Int. Cl.⁶ .................................................. A61K 38/49
[52] U.S. Cl. .................... 424/94.2; 424/94.3; 424/94.63; 424/94.64; 424/94.65; 514/514; 435/212; 435/215; 435/219; 435/188
[58] Field of Search ................................. 424/94.2, 94.3, 424/94.63, 94.64, 94.65, 426, 485, 488, 484, 447, 449; 514/54; 435/212, 215, 219, 221, 188

[56] References Cited

U.S. PATENT DOCUMENTS

| | | | |
|---|---|---|---|
| 3,860,702 | 1/1975 | Buell | 424/94.2 |
| 4,122,158 | 10/1978 | Schmitt | 424/94.3 |
| 4,141,973 | 2/1974 | Balazs | 514/54 |
| 4,226,854 | 10/1980 | Klein et al. | 424/94.65 |
| 4,305,926 | 12/1981 | Everse et al. | 424/94.63 |
| 4,361,551 | 11/1982 | Galbraith | 424/94.65 |
| 4,524,065 | 6/1985 | Pinnell | 424/94.2 |
| 4,532,129 | 7/1985 | Comi et al. | 424/94.63 |
| 4,552,760 | 11/1985 | Murakami et al. | 435/212 |
| 4,613,502 | 9/1986 | Turková et al. | 424/94.3 |
| 4,889,722 | 12/1990 | Sheffield et al. | 514/21 |

FOREIGN PATENT DOCUMENTS

| | | |
|---|---|---|
| 857297 | 12/1970 | Canada . |
| 2488797 | 2/1982 | France . |
| 8402274 | 6/1984 | WIPO ................................. 424/94.1 |

OTHER PUBLICATIONS

Lupashko, cited in Chem. Abstracts vol. 96:62651d, 1982.
Groves, Parenteral Suspensions, in *Parenteral Products* ©1973 Wm. Heinemann Medical Books Ltd., London, p. 26.
James, et al., *J. Path. Bact.* 90: 279–287 (1965).
H. Ellis, Surgery, Gynecology & Obstet., vol. 133: 497–511 (1971).
Gustavsson, et al., "Plasmin in the Prevention of Adhesions", 327–333 (1955).
Snyder, et al., Arch Ophthalmol., vol. 105: 1277–1280 (1987).
Cassels, et al., *Biochem J.*, vol. 247: 395–400 (1987).
Kane, Annals of Clinical and Lab. Science, vol. 14 No. 6: 443–449 (1984).
White, *Chest*/95: 265S–269S (1989).
Hollander, CRC Critical Reviews in Biotech., vol. 6, Is. 3: 253–271 (1987).
Wun, *CRC Critical Review in Biotechn.*, vol. 8, Is. 2: 131–148 (1988).
Samama, et al., Fundam. Clin. Pharmacol. 2: 509–523 (1988).
Snyder, et al. *Arch. Ophthalmol.*, 105 1277 (1987).

*Primary Examiner*—Jacqueline M. Stone
*Attorney, Agent, or Firm*—Walter H. Dreger

[57] ABSTRACT

A method and pharmaceutical composition for the prevention of fibrin deposition or adhesion formation by topical application of a composition to a site of potential fibrin deposition or adhesion formation comprising a sparingly soluble enzyme that is continuously released at that site for a period of time of from about three days to two weeks which may include an inert adherence enhancing vehicle.

10 Claims, 2 Drawing Sheets

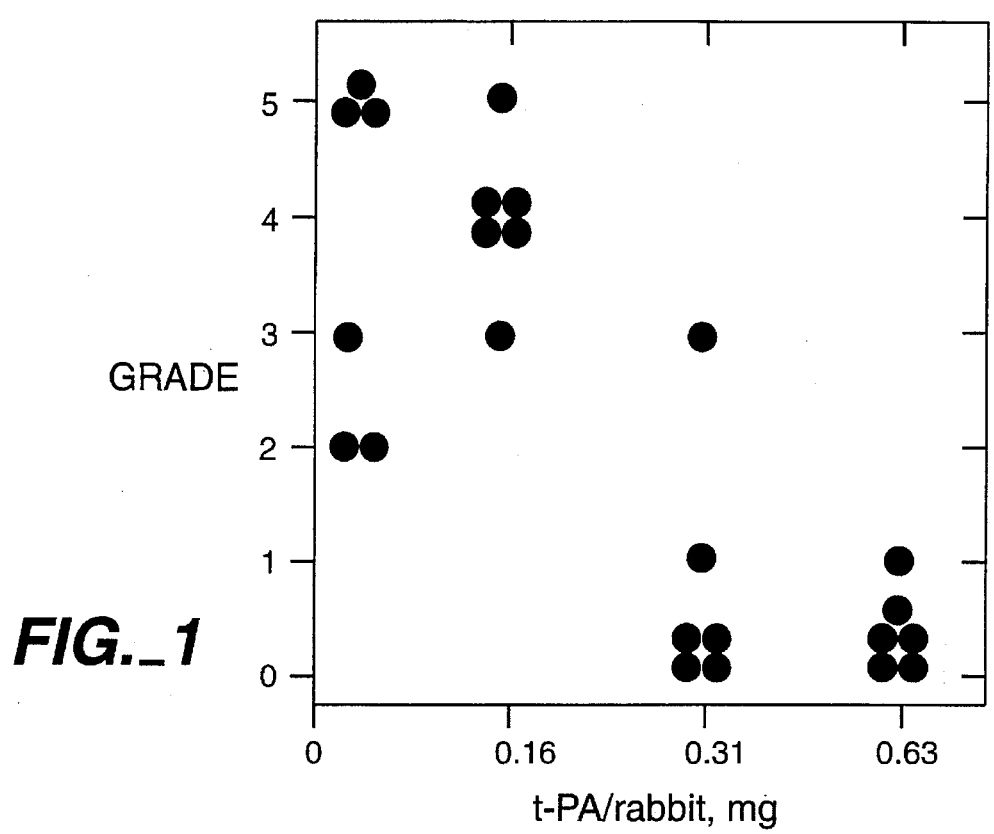
*FIG._1*
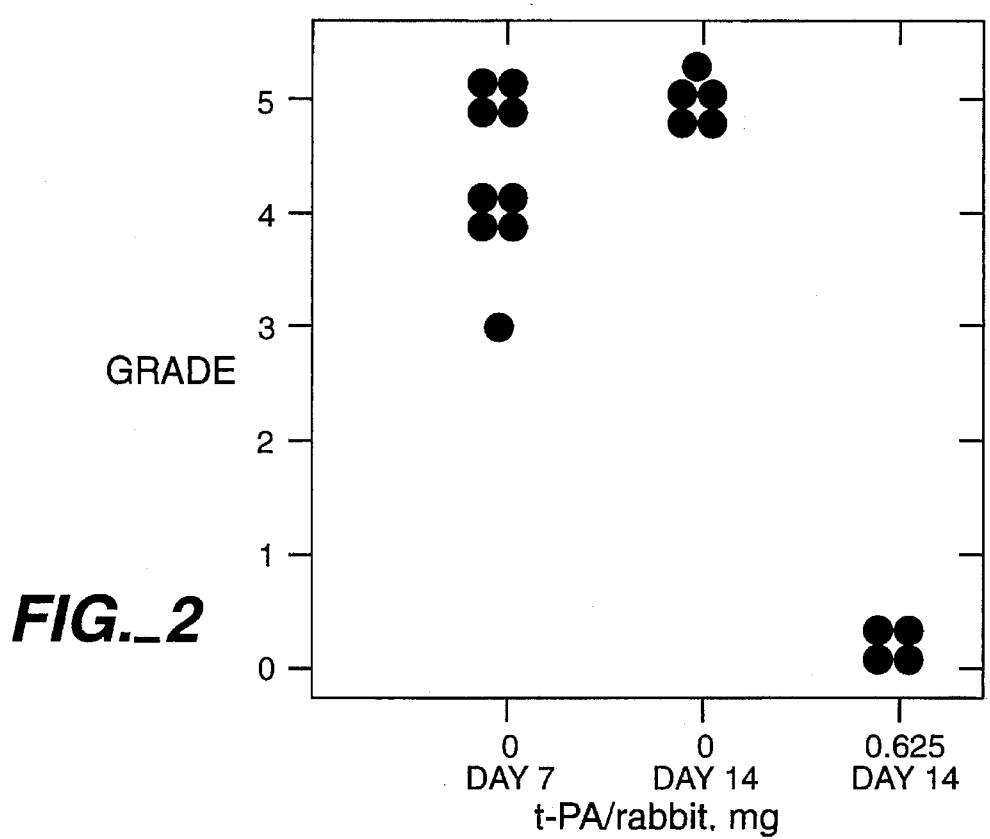
*FIG._2*

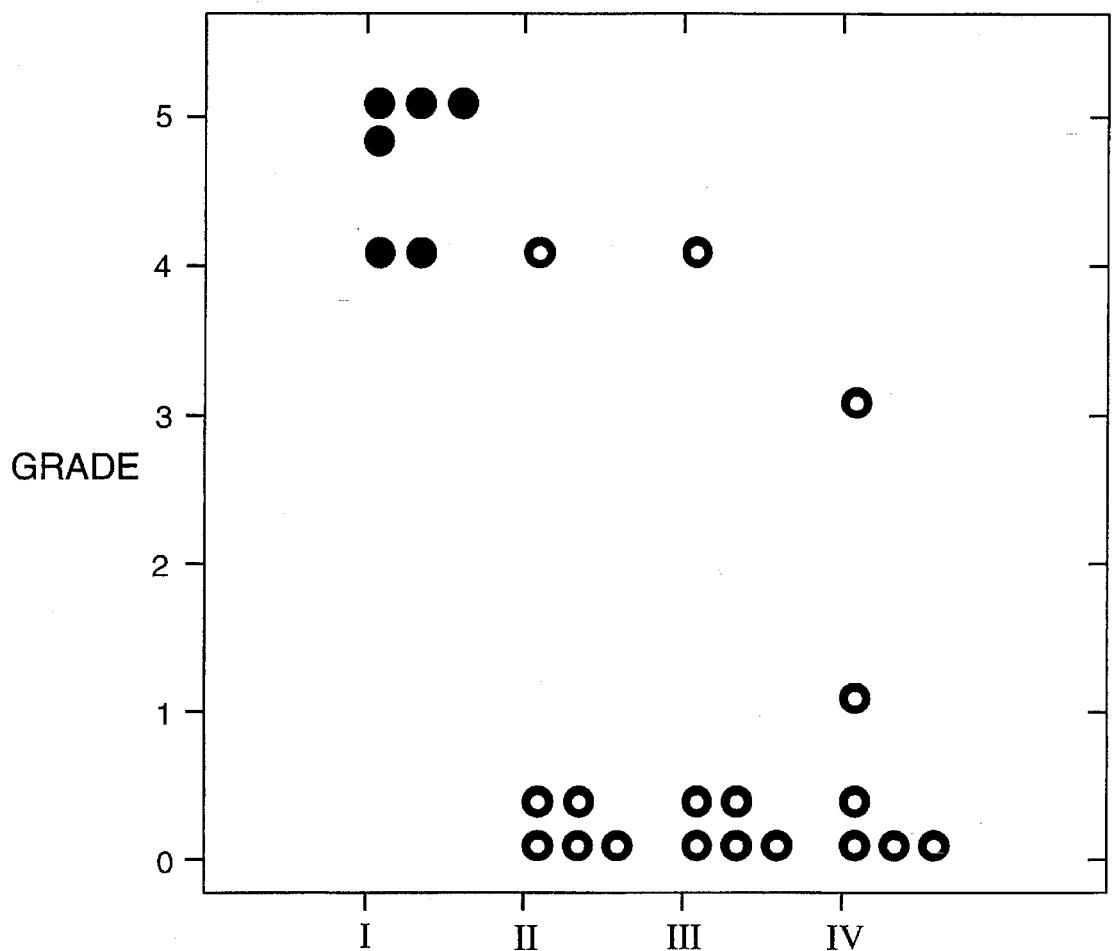

I = HA CONTROL (2.8% HA, 5% glycerol IN 0.01 M NaP04, pH 6.0)
II = 0.06 mg t-PA/gr HA   SLIGHT sub/q (2/6)
III = 0.125mg t-PA/gr HA   SLIGHT sub/q (3/6)
IV = 0.25mg t-PA/gr HA   SLIGHT sub/q (4/6); MODERATE (2/6)

GRADE 5 = AREA GREATER THAN
         ISCHEMIC PATCH COVERED WITH ADHESION
GRADE 4 = 100% OF ISCHEMIC PATCH COVERED WITH ADHESION
GRADE 3 = 50% OF ISCHEMIC PATCH COVERED WITH ADHESION
GRADE 2 = 25% OF ISCHEMIC PATCH COVERED WITH ADHESION
GRADE 1 = <10% OF ISCHEMIC PATCH COVERED WITH ADHESION
GRADE 0 = NO ADHESION

*FIG._3*

METHOD AND THERAPEUTIC COMPOSITIONS FOR THE PREVENTION OF FIBRIN DEPOSITION OR ADHESIONS

This application is a continuation, of application Ser. No. 125,319, filed Nov. 25, 1987, now abandoned, which is a Continuing Application of U.S. Ser No. 07/068,872 filed Jul. 1, 1987 now abandoned.

FIELD OF THE INVENTION

This invention relates to methods and compositions for preventing formation or reformation of adhesions, particularly in the peritoneal or pelvic cavities, resulting from surgery, infection, inflammation or trauma. The invention applies to human and veterinary applications.

BACKGROUND

The formation of postoperative intraperitoneal adhesions, the pathological adherence of organs and tissue surfaces, is the leading cause of intestinal obstruction following abdominal surgery (H. Ellis, Surg. Gynec. Obstec., 133 [1971]). An adhesion typically comprises organized fibrinous exudate projected on the surface of a serous membrane which connects or adheres the opposing surfaces of tissues or organs. It is also the major factor contributing to infertility after reconstructive tubal surgery (Buttram, V. C., Fert. and Ster. 40:5 [1983]). It has been reported that 50–90% of all persons undergoing abdominal surgery develop adhesions (Colleti, L. and Bassart, B. Arch. Surg. Fert. 88: 774 [1964]). Adhesion formation has also been observed following intraabdominal infection (Hau, T. et al., Surg. Gyn. & Ob. 148:415–418 [1979]). Adhesion formation has also been observed following tendon surgery (Weiss, C. et al., Bull. Hosp. Joint Diseases 47(1), 31 [1987].).

From the earliest days of abdominal surgery, surgeons became aware of fibrinous adhesions which stuck loops of intestinal and other abdominal viscera to one another within a few hours of surgery, inflammation or trauma. The fibrinous exudate can either reabsorb completely, leaving a clear peritoneal cavity, or become organized with an in growth of capillaries and fibroblasts to form established fibrous adhesions. The important question, which to this day remains unanswered, is what factor determines whether or not the fibrinous exudate is absorbed or organized. A theory has been developed that adhesion formation is a consequence of the destruction of the peritoneal endothelium. Numerous studies have refuted this theory. (See e.g., Ellis, H. Brit. J. Surg., 50:10 [1962]).

It has been shown that normal healing of peritoneal injuries or defects commences with formation of a fibrin matrix, followed by phagocytosis of that matrix by macrophages, monocytes, lymphocytes and polymorphs. Fibroblasts and collagen bundles are observed prior to the peritoneum taking on a normal appearance. The normal healing process takes approximately three (3) days. (Buckman, R. F. et al., J. Surg. Res. 21, 67 [1976]). Whether the fibrin matrix is reabsorbed appears to be related to whether the tissue was ischemic (Rubin, i.C., Surg. Obstet., 12:117 [1911]). Ellis, H. et al., Brit. J. Surg. 52:471 (1965) developed an ischemic peritoneal model and showed that 83% of ischemie injuries resulted in adhesion formation while only about 9% of the, non-ischemic models produced adhesions. Using electron microscopy, the fibroblastic invasion has been shown to arise from macrophages which infiltrate the area, and develop into fibroblasts, giant cells, and epithelial-like cells. (Eskeland, G., Acta Path. Microbiol. Stand., 62:459 [1964]). Adhesion formation according to Ellis acted as a vascular graft. Using a similar model to Ellis, Buckman et al., supra., showed that peritoneal defects have a high plasminogen activity which is lost in peritoneum rendered ischemic.

Fibrin deposition following bacterial infiltration of the peritoneal cavity is a defense mechanism in preventing septicemia. (Ahrenholz, D. H. and Simmons, R. L., Surgery 88: 41–47 [1980], Zinser, H. H. and Pryde, A. W., Ann. Surg. 136: 818 [1982]). The bacteria are contained, but the fibrin deposition often leads to abscess formation. (Ahrenholz and Simmons, supra.). Fibrin deposition occurs during early stages of peritonitis, when fibrinogen-rich exudate in the peritoneal cavity is converted to fibrin. (Hau, supra.). Postoperative intraabdominal abscesses are a potential source of infection and, ultimately, death. Peritonitis and its complications are associated with a high mortality rate. Amongst the elderly the mortality rate is in the range of 60–80%. (Hau, T. et al., Curr. Prob. Surg. 16: 1–65 [1979]).

Plasminogen activators present in both the mesothelium and submesothelial blood vessels of the peritoneum are responsible for lysing and removing intraperitoneal fibrin deposits. (Porter, J. M. et al., L. Surg. Forum 20:80 [1969]; Buckman, R. F. et al., J. Surg. Res. 20:1 [1976]). Serosal or peritoneal injury such as inflammation or trauma results in the formation of an exudate of cellular components and fibrin through tears in the small veins of the traumatized area (Aurora, A. L. et al. Indian J. Med. Res. 62: [1972]) as well as a local decrease in fibrinolytic activity. (Buckman, R. F. supra.) It has been shown that when local fibrinolytic activity is reduced by 50% or more, fibrin cannot be cleared and permanent adhesions form. (Gervin, A. S. et al., Am. J. Surg. 125 [1973]).

Numerous papers have been published describing efforts to prevent adhesion formation. Various prophylactic methods have been tried to prevent fibrin deposition and adhesions. Prevention of the deposition of fibrin in the peritoneal exudate has involved the use of sodium citrate, heparin, and other anticoagulants. In removal of the fibrin which already has formed, a variety of enzymes have been used, for example, trypsin, pepsin, papain, hyaluronidase, streptokinase and streptodornase. Other approaches for fibrin removal use such salts as sodium ricinoleate or lavage for mechanical removal of fibrin.

Heparin and dicumarol were the first agents used to prevent fibrin deposition. (Lehman, E. P. and Boys, F. Ann. Sur., 112:969 [1940]; White, B. H. Ann. Surg., 130:942 [1949]). Deaths and postoperative hemorrhage were reported in those patients receiving heparin. More recently, the antithrombogenic property of dextran has led to its use to prevent adhesions. (Choate, W. H. et al., Arch. Surg., 88:249 [1964]). Intraperitoneal dextran was found to decrease the severity of the adhesions but did not prevent formation (Kapur, B. M. L. et al., Indian J. Med. Res., 56:1406 [1968]). Oral administration of the anti-inflammatory agent oxyphenbutazone was also used to reduce adhesion formation. (Kapur, B. M. L., et al., Arch. Surg., 98:301 [1969]).

Lavage with saline, dextrose, or particularly a hypertonic dextrose solution has been suggested, but the rapid absorption of such solutions rendered them ineffective. (Buchbinder, J. R., Surg. Gynec. Obstet., 45:769 [1927]; Totten, H. P., Surgery, 8:456 [1940]). Digestive enzymes such as pepsin and trypsin were thought to have utility by destroying fibrin. However, these substances are both rapidly neutralized by peritoneal exudates and were shown to be ineffective. (Kubota, T., Japan M. World, 11:226 [1922]). Papain a proteolytic enzyme was also tried but found to be neutralized by the peritoneal exudate. Papain was also administered orally and found to reduce the severity of the adhesions, but not the incidence. (Kapur, B. M. L., et al., Arch. Surg., 98:301 [1969]). Intraperitoneal administration of papain in rats had no effect on adhesion formation. (Stevens, L. E., Amer. J. Surg., 115:535 [1968]).

A number of fibrinolytic agents have been tested to prevent adhesions. The fibrinolytic system is typically understood to mean that system in blood which involves the conversion of plasminogen to plasmin. A natural plasminogen activator interacts with plasminogen to convert the precursor to plasmin which then lyses cross-linked fibrin. Exogenous activators such as streptokinase and urokinase also activate the conversion of plasminogen to plasmin. Thrombolytic agents include plasmin, and plasminogen activators such as streptokinase, streptodornase, and urokinase. These thrombolytic and fibrinolytic agents as well as other agents have been used to prevent fibrin deposition and remove adhesions. Initial work showed that streptokinase and streptodornase prevented traumatically induced adhesions in rabbits, but not in dogs. (Wright, L. T., et al., Proc. Soc. Exp. Biol. Med., 75:602 [1950]). In one study, it was observed that intraperitoneal therapy on three successive days was more effective than a single injection. (Knightly, J. J., et al. Surgery, 52:250 [1962]). Other studies were less favorable. In a series of experiments using intravenous and intraperitoneal administration of a variety of fibrinolytic enzymes in dogs, rabbits, and rats as well as different techniques to produce adhesions, no significant prophylactic or therapeutic effect was observed. (Jewett, T. C., et al., Surgery 57:280 [1965]). Highly purified preparations of streptokinase administered to rats in a single dose or multiple single injections on three successive days did not inhibit adhesion formation. (James, D. C. O., et al., J. Path. Bact. 90:279 [1965]). Additional studies using purified streptokinase in rabbits indicated that adhesions to areas of parietal injury could be inhibited by giving multiple injections of streptokinase in solution intraperitoneally on two or three consecutive days. (Id.) Thrombolytic therapy has been used to prevent fibrin deposition in endocarditis in a rabbit model. (Duraug, D. T., J. Path. 129:537 [1975]). Fibrinolytic agents have been used to reduce wound infections induced by infected plasma clots in guinea pig skin incisions. (Rodeheauer, G. et al., Am. J. Surg. 129:537–544 [1975]).

Other compounds which were observed to have a fibrinolytic effect have also been used to prevent adhesions. Protoporphyrin, which has a fibrinolytic action, was found to reduce the percentage of adhesions developing to laparotomy in the rat. (Iijima, N. et al., Postgrad. Med. J. 46:278 [1970]). Hyaluronidase, an enzyme which hydrolyzes hyaluronic acid, one of the polysaccharides constituting intercellular ground substance, has prevented adhesion formation in dogs when administered intraperitioneally at the same time that talc was applied to induce adhesion formation. (Connolly, J. E. and Richards, V. Surg. Forum, 2:85 [1951]). Other studies in rat following cecal crushing showed no reduction in the incidence of adhesions following intraperitoneal administration of hyaluronidase. (Thomas, J. et al., Proc. Soc. Exp. Med., 74:497 [1950]).

Dexamethasone, methylprednisolone, sodium succinate, promethazine hydrochloride and human fibrinolysin alone and in combination were administered intramuscularly or intraperitoneally to rats to prevent adhesion formation. (Gazziniga, A. G. et al., Arch. Surg. 110:429 [1975]). None of the agents alone eliminated adhesion formation. Methylprednisolone, promethazine and human fibrinolysin in combination intraperitoneally in a single dose appeared to eliminate adhesion formation. Id.

In addition to those substances mentioned above, others have been placed in the peritoneal cavity to prevent adhesion formation, including minced ox peritoneum, olive oil, eptnephrine solution, amniotic fluid and sodium ricinoleate. None of the substances have been shown to prevent adhesion formation or reformation.

An object of the present invention is to provide a composition preventing fibrin deposition or adhesion formation for use in various surgical and clinical contexts including, but not limited to, abdominal and pelvic surgery, abdominal infection, inflammation or trauma. Another object of the invention is to provide a composition that is easy and convenient to apply to the site of potential fibrin deposition or adhesion formation. Yet another object of this invention is to provide a method of preventing fibrin deposition or adhesion formation by topical application of the composition of this invention to the organs and/or surrounding tissues to which fibrin may be deposited or an adhesion may form. Still another object of this invention is to eliminate the introduction of nondegradable solids as a means for delivering agents for preventing fibrin deposition or adhesion formation. Another object is to provide enzymes for the prevention of fibrin deposition or adhesions in a form such that they are not inactivated by substances in the biological fluid. Yet another object is to provide such enzymes in a formulation enabling continuous release without any need for exogenous matrices or devices.

SUMMARY OF THE INVENTION

The objects of this invention are accomplished by topical administration of an enzyme in sparingly soluble form permitting continuous application of the enzyme to the site of potential fibrin deposition or adhesion formation. A sparingly soluble form for administration of an enzyme effective in fibrinolysis or thrombolysis is useful for the treatment of adhesion particularly following surgery, infection, trauma or inflammation when administered topically to the site of potential fibrin deposition or adhesion formation such that the enzyme is continuously available at the site for at least about three days. The enzyme is delivered preferably in sparingly soluble form as suspended solid particles in an inert adherence enhancing vehicle facilitating delivery of the enzyme over a prolonged period of time. It was not appreciated until the instant invention that a single topical application of a sparingly soluble solid enzyme to a site would provide continuous delivery of that enzyme to prevent fibrin deposition or adhesion formation. Preferably, the enzyme for use herein is dialysis precipitated tissue plasminogen activator. Accordingly, in one aspect, the invention is directed to a pharmaceutical composition comprising a sparingly soluble enzyme, such as tissue plasminogen activator, to prevent adhesion formation in various contexts, such as following surgery or infection. In another aspect, the invention is directed to a method of treatment of clinical fibrin deposition of adhesions and the use of such compositions in such a method.

BRIEF DESCRIPTION OF THE DRAWINGS

FIG. 1. Effect of doses of recombinant tissue plasminogen activator on the prevention of adhesion formation in rabbits. Varying amounts of recombinant tissue plasminogen activator in 2.5 grams of a semisolid vehicle were applied to the traumatized areas of tissue in the peritoneum. After one week the animals were euthanized and the extent of the adhesions were scored. The number of rabbits with adhesions at a dosage of 0.125 and 0.25 mg of recombinant tissue plasminogen activator/gm of gel was significantly ($p<0.01$) different from the control and 0.062 mg of recombinant tissue plasminogen activator/gm of gel groups as determined by the Mann Whitney non parametric test.

FIG. 2. Effect of recombinant tissue plasminogen activator on the prevention of re-formation of adhesions after surgical lysis. The extent of the adhesions formed in rabbits with no treatment is shown at day 7. After surgical lysis of the adhesions which formed, the animals were divided into two groups; control animals received vehicle only and the treated animals received 0.25 mg of recombinant tissue plasminogen activator/gm of gel. At day 14 the number of animals which received recombinant tissue plasminogen activator had a dramatic decrease in the extent of the adhesions which reformed.

FIG. 3. Effect of doses of recombinant tissue plasminogen activator on the prevention of adhesion formation in rabbits. Varying amounts of recombinant tissue plasminogen activator in 2.5 grams of a sodium hyaluronate 2.8% gel were applied co the traumatized areas of tissue in the peritoneum. After one week, the animals were euthanized and the extend of the adhesions were scored.

DETAILED DESCRIPTION

As used herein, "a sparingly soluble enzyme" is an enzyme in a molecular form which dissolves at a desired rate in a biofluid capable of preventing fibrin deposition or adhesion formation by a single topical application to a site of potential fibrin deposition or adhesion formation. The enzyme is applied to the site of potential fibrin deposition or adhesion formation as a solid, for example as a powder, slurry or suspension. "Sparingly soluble" refers to the relatively low solubility of the enzyme in biofluids, for example plasma, interstitial or peritoneal. The rate of dissolution is selected so that the enzyme will dissolve in the biological fluid over a period sufficient to prevent fibrin deposition or the formation or reformation of an adhesion at the target site typically about three to fourteen days. Dissolution of the sparingly soluble enzyme at the site of potential fibrin deposition or adhesion formation over a period of time is due to that relatively low solubility. This sustained dissolution over a period of time enables a single topical application to provide continuous release of active enzyme over the desired period of time. Included within the enzymes for use herein are thrombolytic or fibrinolytic enzymes, such as plasmin, streptokinase, urokinase, tissue plasminogen activator and streptodornase. Fibrinolytic enzymes include enzymes which convert plasminogen to plasmin including streptokinase, urokinase, and plasminogen activator or which digest fibrin directly. Thrombolytic agents include fibrinolytic enzymes as well as other proteolytic enzymes. Such a proteolytic enzyme is brinase. A preferred sparingly soluble solid enzyme is "tissue plasminogen activator" which as used herein refers to an enzyme that may be extracted and purified from natural sources, or obtained using recombinant means. The enzymes of this invention thus may be obtained from mammalian, bacterial or yeast sources. It is preferred that the homologous enzyme for the species to be treated be used. For example, canine enzyme, in accord with this invention, can be used to prevent adhesion formation in dogs. Also included within the scope of the solid enzyme are variants having amino acid substitutions and/or deletions and/or additions, organic and inorganic salts and covalently modified derivatives of tissue plasminogen activator.

The term "solid" describes the state of the enzyme at the time of application to the site of potential adhesion formation. The enzyme is in a homogeneous form and appears in the case of tissue plasminogen activator as a white, amorphous powder. The solid state of the enzyme is obtained using various methods known to the ordinarily skilled artisan for example dialysis, precipitation or lyophilization. Precipitation of the enzyme can be achieved, for example, by varying the pH, composition of co-solvent, temperature, and salt.

The composition of this invention comprises a therapeutically effective amount of a sparingly soluble enzyme in, for example, powdered form. The composition may additionally include an inert adherence enhancing vehicle. The composition of this invention is applied directly to the site of potential fibrin deposition or adhesion formation for continuous release of the enzyme to that site for a period of time. Suspension of the enzyme in an inert non-toxic adherence enhancing vehicle reduces the likelihood of degradation by endogenous proteases. The adherent quality of the inert vehicle enables retention of the solid enzyme at the site of application. This enables localized continuous release of the enzyme at the site of application over a period of time. "Continuous" refers to the uninterrupted, unbroken release of the enzyme at the site of application for a desired period of time. Thus, the novel formulation limits the water accessibility to the solid enzyme, limits degradation and enables a slower release rate.

The sparingly soluble enzyme may be administered at a dosage sufficient to prevent fibrin deposition or formation of adhesions following surgery, infection, trauma, or inflammation. Therapeutically effective amounts of the sparingly soluble enzyme will be administered in accord with the teaching of this invention. For example, therapeutically effective amounts of streptokinase in a sparingly soluble form are in the range of about from 300 units/gm of gel to 12,500,000 units/gm of gel. A preferred therapeutic amount of streptokinase is in the range of about 10,000 units/gm of gel to about 375,000 units/gm of gel. In the case of tissue plasminogen activator in a solid form, therapeutically effective amounts are in the range of about from 0.02 mg/gm of gel to 25 mg/gm of gel. A preferred therapeutic amount of tissue plasminogen activator is in the range of about 0.20 mg/gm of gel to 2.5 mg/gm of gel. A most preferred therapeutic amount of tissue plasminogen activator is in the range of about 0.25 mg/gm of gel to about 1.0 mg/gm of gel.

An adherence enhancing vehicle is defined as a semisolid, mucilaginous pharmaceutically inert carrier for positioning the sparingly soluble enzyme at the site of potential adhesion formation. The vehicles are inert, non-toxic, non-irritating and are physiologically and pharmaceutically acceptable. The vehicles generally are bioerodable since they are worn away from the site of application as compared to biodegradable vehicles which are chemically broken down. The inert adherence enhancing vehicles ensure continuous delivery of the solid enzyme at the site of application while reducing the appearance of the enzyme at undesirable locations, e.g. in the blood. The sparingly soluble form of the enzyme may possess adherent qualities such that the use of an inert adherence enhancing vehicle is unnecessary. Long chain hydrocarbons or vegetable oils and waxes composed of mixtures of saturated and unsaturated fatty acid glycerides or mixtures of modified saturated and unsaturated fatty acid glycerides may be used as such inert adherence enhancing vehicles or carriers. Such vehicles or carriers include, but are not limited to, semisolid vehicles such as petrolatum jelly or semi-synthetic glycerides, polyhydroxy solvents, such as glycerol, long chain hydrocarbons, bioerodable polymers or liposomes. Included within bioerodable polymers are low molecular weight polymers which can be formulated in semi-solid form. Such formulated semisolid polymers include poly(esters), polyamides, poly(amino acids), polyacetals, polyanhydrides, poly(ortho ester)s and polysaccharides such as hyaluronic acid. The inert non-toxic vehicles of this invention should not include biodegradable or nondegradable solids other than the sparingly soluble enzyme since it has been observed that application of powders such as magnesium silicate, talc and starch cause adhesion formation (Corson, S. L., J. Reprod. Med., 29(3), 143[1984]).

The sparingly soluble form of the enzyme may be dispersed in the pharmaceutically inert adherence enhancing vehicle to achieve a rate of dissolution at the site of application. The sparingly soluble form controls the release into the biofluid permitting activity over a desired period of time. This is in contrast to a soluble form of the enzyme which would be available for a shorter period of time. The release of the enzyme can be predicted from its solubility and particle size as shown below. For a monolithic vehicle, where the enzyme is dispersed as solid particles within an inert matrix, the rate of release of the enzyme is given by the equation:

$$\frac{dM}{dt} = \left(\frac{2A - C_s}{2}\right) dx$$

and the amount released at any time after administration can be approximated by the equation:

$$M = (2ADC_s t)^{1/2}$$

In these equations, M is the amount of enzyme released, A is the drug loading per unit mass of vehicle, $C_s$ is the solubility of the enzyme in the vehicle, D is the diffusion coefficient of the enzyme, t is time and dx the thickness of the enzyme depleted zone within the matrix (T. Higuchi, J. Soc. Cosmetic Chemists 11, 85 [1960]; T. Higuchi, J. Pharm. Sci. 50, 874 [1961]). Consequently, the release rate from this type of formulation can be modified by varying $C_s$, the solubility of the enzyme (e.g. using different types of vehicles) or by controlling the drug loading in the vehicle.

When the enzyme is suspended as solid particles in a water soluble vehicle, the rate of release of the protein can be described by the classical Noyes-equation:

$$\frac{dM}{dt} = \frac{Da}{h}(C_s - C)$$

Here, M is the amount released or dissolved, t is time, D the diffusion coefficient of the drug molecules in the medium, a the exposed surface area, h the thickness of the diffusion layer $C_s$ and C are the solubility and the concentration of the enzyme at the site of application. In the case of solid particles of enzyme placed in a rapidly dissolvable vehicle, dissolution of the vehicle in the interstitial space will leave a dispersion of the enzyme in that space. The enzyme being relatively insoluble will dissolve over a desired period of time depending on its solubility and particle size.

According to this equation, the rate of release of sparingly soluble enzyme from a water soluble vehicle can be controlled by varying a, the exposed particle surface area. This can be achieved by controlling the particle size. Larger particles result in smaller surface area and slower release rate, whereas small particles have increased total exposed surface and should yield higher release rate.

The sparingly soluble enzyme is not so insoluble to be present in the biofluid for an extremely long time with very low activity. The low solubility form ensures continuous release over the desired period of time. This continuous release may also be promoted by use of an inert vehicle. The preferred vehicles are those which provide for release of the enzyme over the desired period. The period of time over which the enzyme is continuously released is at least about three days to about two weeks. The preferred period of time over which the enzyme is released is at least about four days to about ten days.

Administration of the enzyme composition of the instant invention may be made prior to surgical suturing. In the case of abdominal surgery the composition of this invention that is the sparingly soluble enzyme alone or in an inert adherence enhancing vehicle will be applied by hand or massage or some other suitable method, for example, via a laparoscope, in a thin film on the abdominal organs prior to drawing the omentum over the organs before suturing. It would be apparent to the surgeon of ordinary skill those organs to which the composition should be applied. For example in the case of abdominal surgery the small bowel, which may be the site of obstruction consequent to adhesion formation, would be one likely site of application. The amount of composition to be applied will be as described above, subject to clinical experience such as the extent of injury, type of surgery, condition of the patient, thrombolytic activity of the enzyme and such other factors as would be appreciated by the ordinarily skilled physician.

EXAMPLE 1

Materials and Methods

1) Rabbit Model

The strongest stimulus to adhesion formation has been shown to be the presence of ischemic tissue which results from suturing or patching peritoneal defects rather than stripped peritoneal surface. New Zealand white rabbits (approx. 3.0 kg) were anesthetized with Fluanizone and Fentanyl, and midline laparotomies were performed using clean operative techniques. A nine $cm^2$ area of the peritoneal wall was removed and resutured in place at the corners with silk sutures, creating an ischemic patch of peritoneal tissue. A proximal area of the cecum (approx. 75 $cm^2$) was abraded with dry gauze until punctate bleeding occurred. An insoluble or relatively insoluble enzyme having thrombolytic or fibrinolytic activity was delivered to the ischemic tissue either as a film by the method of the invention directly to selected organs or as a lavage (0.5 mg tissue plasminogen activator/150 ml isotonic saline solution), or through a vascular access port which delivers the drug solution directly to the resutured peritoneal tissue via external application of a formulation over the area (2.5 gm of gel containing 0.25 mg of tissue plasminogen activator/gm of formulation). After replacement of the cecum into the abdominal cavity, the muscle layer of the abdomen was sutured closed with 1.0 proline and the skin layer closed with 2.0 proline. After seven days, the rabbits were euthanized and repeat laparotomies were performed to determine the extent of adhesions formed. The criteria established for a positive adhesion was adherence of the cecum to the ischemic patch of tissue on the peritoneal wall. The following scoring system was used to evaluate the severity of adhesions:

Grade 0=no adhesion observed

Grade 1=less than 10% of ischemic patch covered with adhesion.

Grade 2=25% of ischemic patch covered with adhesion.

Grade 3=50% of ischemic patch covered with adhesion.

Grade 4=100% of ischemic patch covered with adhesion.

Grade 5=area greater than ischemic patch covered with adhesion.

2) Tissue Plasminogen Activator Bulk Powder

Tissue plasminogen activator bulk powder was prepared by dialyzing out the solubilizing buffer from a stock solution. Thus, 1000 ml of a solution containing 2.5 mg/ml tissue plasminogen activator, 87.1 mg/ml L-arginine, 26.8 mg/ml phosphoric acid (85% w/w), and 0.1 mg/ml polysorbate 80 were divided into 100 ml portions and transferred into dialysis membrane tubings (Spectrapor membrane tubing 6000–8000 MW cutoff). Each portion was dialyzed against 1000 ml of purified and sterile water at 5° C. After four changes of dialysate, the protein precipitate inside of the tubing was collected. Following centrifugation (4000 rpm for 15 minutes at 5° C. in a Beckman Accu-spin refrigerated centrifuge) and decantation of the supernatant liquid, purified and sterile water was added to the tube. The protein was rinsed by means of a mixer (Vortex mixer), and separated again by centrifugation. This operation was repeated three more times. After the final rinse, tissue plasminogen activator was collected and lyophiltzed. The product obtained was a white, amorphous powder.

3) Dosage Form Preparation

Various aqueous solutions similar to those used in the art were also prepared and tested, for example using colloidal polysaccharides such as dextran or modified cellulose gums (Formulations 1 and 2 of section 4), modified collagen or poloxamers (Formulations 3 and 4 of section 4) and glycerol thickened by addition of polyethylene glycol polymers (Formulation 5 of section 4). Formulations 1–4 fall into two categories: tissue plasminogen activator solubilized in an aqueous gel (Formulations 1 and 3); and tissue plasminogen activator suspended as sparingly soluble particles in an aqueous gel (Formulations 2 and 4).

Formulation 1:

| A-Buffer Solution | |
|---|---|
| L-arginine | 3.48 gm |
| $H_3PO_4$ (85% w/w) | 1.54 gm |
| Purified water QS | 100 gm |

L-arginine was dissolved in 90 ml of purified water. Phosphoric acid (1.54 gm) was added slowly to obtain a solution of pH 6.0. The volume of the solution was brought to 100 ml with purified water. This solution was put through a sterifilter of 0.22 µm filterpore size (Millex-GV or equivalent) and stored at 5° C.

| B-Final Formulation: | |
|---|---|
| Dextran (KW 2 000 000) | 0.1–0.5 gm |
| Tissue plasminogen activator | 0.00025 gm |
| Buffer solution A QS | 1.00 gm |

Tissue plasminogen activator was added and dissolved in buffer solution A. Dextran was then added slowly with vigorous mixing to dissolve the polymer until a homogeneous solution was obtained.

Formulation 2:

| Dextran (MW: 2,000,000) | 0.1–0.3 gm |
|---|---|
| Tissue plasminogen activator - sparingly soluble particles | 0.00025 gm |
| Purified water QS | 1.00 gm |

Dextran was dissolved in water with vigorous mixing until a homogeneous solution was obtained. Tissue plasminogen activator was added to the solution, mixed and the protein was dispersed to homogeneity.

Formulation 3:

| A-Buffer Solution | |
|---|---|
| L-arginine | 3.48 gm |
| $H_3PO_4$ (85% w/w) | 1.54 gm |
| Purified water QS | 100 gm |

L-arginine was dissolved in 90 ml of purified water. Phosphoric acid was added slowly to obtain a solution of pH 6.0. The amount was approximately 1.54 gm. The volume of the solution was brought to 100 ml with purified water. This solution was put through a sterifilter of 0.22 µm filterpore size (Millex-GV or equivalent.) It was then stored at 5° C. and used in the preparation of the final formulation.

B- Final Formulation:

| Poloxamer 407 | 0.05–0.3 gm |
|---|---|
| Soluble tissue plasminogen activator | 0.00025 gm |
| Buffer solution A QS | 1.0 gm |

Buffer solution A was chilled to 5° C., tissue plasminogen activator was added dissolved. The poloxamer was then added and dissolved with vigorous mixing until a homogeneous solution was obtained. The solution was run through a sterifilter of 0.22 µm pore size (Millex-GV or equivalent).

Formulation 4:

| Poloxamer 407 | 0.05–0.3 gm |
|---|---|
| Tissue plasminogen activator - sparingly soluble particles | 0.00006 gm |
| Purified water QS | 1.00 gm |

Water was chilled to 5° C., poloxamer 407 was added and dissolved with vigorous mixing until a homogeneous solution was obtained. Tissue plasminogen activator was added and homogeneously dispersed.

Formulations 5–9 are additional examples of the novel compositions of this invention, and can be classified into three broad categories: tissue plasminogen activator suspended as sparingly soluble particles in an anhydrous, water soluble gel (Formulation 5); tissue plasminogen activator suspended as sparingly soluble particles in a long chain hydrocarbon base (Formulation 6); and tissue plasminogen activator suspended as sparingly soluble particles in a bioerodable, semi-synthetic oil and wax composed of mixtures of unsaturated and saturated fatty acid glycerides (Formulations 7, 8 and 9).

Formulation 5:

| Polyethylene glycol MW 800–1500 | 0.0–0.3 gm |
|---|---|
| Tissue plasminogen activator | 0.00025 gm |
| glycerol QS | 1.00 gm |

Glycerol was warmed to approximately 35° C. to 45° C. Polyethylene glycol was added and mixed until a homogeneous solution was obtained. Tissue plasminogen activator was added and homogeneously dispersed. The formulation was cooled and congealed at room temperature with continued stirring.

Formulation 6:

| Tissue plasminogen activator | 0.00025 gm |
|---|---|
| white petrolatum QS | 1.00 gm |

Petrolatum was melted at approximately 35° C. to 45° C. Tissue plasminogen activator was added and dispersed to homogeneity. The formulation was cooled and congealed at room temperature with continued mixing.

Formulation 7:

| Tissue plasminogen activator | 0.00025 gm |
|---|---|
| Glycolysed polyoxyethylenised oleic glycerides (Labrafil M1944CS) | 0.05–0.5 gm |
| Glycolysed polyoxyethylenised stearic lauropalmito glycerides (Labrifil M2130CS) QS | 1.00 gm |

Formulation 8:

| Tissue plasminogen activator | 0.00025 gm |
|---|---|
| Glycolysed polyoxyethylenised oleic glycerides (Labrafil M1944CS) | 0.05–0.5 gm |
| Transesterified, saturated fatty acid glycerides (Suppocire AIM) QS | 1.00 gm |

Formulation 9:

| Tissue plasminogen activator | 0.00025 gm |
|---|---|
| Neutral vegetable oil (caprylic/capric triglycerides Miglyol 812) | 0.05–0.5 gm |
| Transesterified, saturated fatty acids glycerides (Witepsol W32) QS | 1.00 gm |

Formulations 7, 8 and 9 were prepared as follows: oils were warmed to approximately 35° C. to 45° C., the solid fatty acid glycerides were added and melted, and the tissue plasminogen activator was added and dispersed homogeneously in the mixture. The formulation was cooled and congealed at room temperature with continued mixing.

EXAMPLE 2

Sparingly Soluble Composition Effect on Peritoneal Adhesions

Adhesion Formation

The animals were treated as described above with tissue plasminogen activator either as solid enzyme or in soluble form. In the case of soluble enzyme, the peritoneal cavity was lavaged one time prior to closure of the incision. The extent of adhesions formed was evaluated after fourteen days. Alternatively, repeated external administrations of the solution to the ischemic site were made via a vascular access port. The extent of adhesion formation for the access port application was examined after five days. Saline solution was used as control in all cases. The results are shown in Table 1.

TABLE 1

| Rabbit Identification | 1 | 2 | 3 | 4 |
|---|---|---|---|---|
| Treatment Method | | Grade | | |
| Lavage with 150 ml saline | 3 | 3 | 0 | 3 |
| Lavage with 150 ml saline containing 0.5 mg tissue plasminogen activator | 2 | 0 | 2 | 4 |
| Vascular access port 5 ml saline/2× daily/5 days | 5 | 4 | | |
| Vascular access port 0.5 mg tissue plasminogen activator/2× daily/5 days | 0 | 0 | 0 | |

All untreated animals developed high scoring adhesions demonstrating that post-surgical adhesion can be generated reproducibly with this model. Rabbits treated with a single lavage showed lower adhesion score on the average than control animals. The improvement was however more pronounced when tissue plasminogen activator was applied directly over the ischemic area twice daily over a period of 5 days. Out of three animals, all three exhibited no sign of adhesion. Both animals in the control group developed grade 4 and 5 adhesion respectively.

Tissue plasminogen activator was incorporated in the novel semisolid formulations in accord with this invention and applied topically over the excised and resutured peritoneal wall area and over the abraded cecum segment. The amount of tissue plasminogen activator applied was kept constant at 0.25 mg tissue plasminogen activator per gm of gel. Approximately 2.5 gm of the novel composition of this invention was applied by hand and massaged to a thin film over the surface of the site of potential adhesion formation.

In most cases studied, control animals treated with formulation placebos containing no tissue plasminogen activator, developed extensive adhesion over the whole traumatized area. Tissue plasminogen activator solubilized and applied as an aqueous gel (Formulations 1 and 3), showed little improvement in preventing adhesion formation as compared to the control group. As in the lavage treatment, solubilized tissue plasminogen activator may be rapidly inactivated in vivo, and its activity not sufficiently sustained to prevent adhesion formation completely. Inhibition of adhesion formation was observed in all other treated groups utilizing the composition of this invention. Only three of 29 animals tested using the novel compositions described in Formulations 5, 6, 7, 8 and 9 developed adhesion. A relatively insoluble enzyme in solid form such as tissue plasminogen activator suspended in a water soluble vehicle (Formulation 5) was also efficacious in preventing adhesion formation suggesting that the limited intrinsic solubility of tissue plasminogen activator is also a factor contributing to the stability of the agent in vivo and the prolonged fibrinolytic activity required for therapeutic effects.

Additional experiments using varying amounts of tissue plasminogen activator were carried out. Twenty-four rabbits (3 kg) were divided into four equal groups. After surgical injury 2.5 grams of vehicle containing a total dose of 0, 0.16, 0.31 or 0.63 mg of recombinant tissue plasminogen activator was applied to the traumatized tissues of each rabbit. The results of the extent of the adhesions formed are summarized in FIG. 1. Although no effect on the extent of adhesion formation by recombinant tissue plasminogen activator in the novel composition of this invention was evident with the lowest dose, a dramatic decrease in the formation of adhesions was seen with both the 0.31 and 0.63 mg.

The severity of the adhesions which formed were characterized further by determining the extent of mechanical force required to separate the adherent tissues. Blunt dissection using, for example, closed scissors to separate the adhered tissue or in the case of severe adhesion actual cutting were the mechanical forces used. These results are summarized in Table 3. The adhesions that formed in the animals treated with the 0.31 and 0.63 mg of tissue plasminogen activator required simple blunt dissection to separate. The adhesions that formed with the low dose or no recombinant tissue plasminogen activator often required more time consuming sharp dissection to separate.

Adhesion Reformation

Although the formulation of this invention comprising a thrombolytic or fibrinolytic agent such as recombinant tissue plasminogen activator and a vehicle can be used to prevent adhesions, it may also be used to prevent the reformation of adhesions following adhesion separation. The following experiment was designed to determine whether the composition of recombinant tissue plasminogen activator influences reformation of adhesions after lysis of adhesions. Ten rabbits were anesthetized and midline laparotomies were performed. An ischemic peritoneal flap was created in the right flank followed by cecum abrasion as described above. No vehicle was applied to the traumatized tissues prior to abdominal closure. After seven days repeat laparotomies were performed. At exploration the adhered structures were separated and all bleeding was controlled by electrocautery. Nine of the ten rabbits had adhesions which were Grade 3 or above. One rabbit had no adhesion and was removed from the study. In four rabbits the separated fibrin coated surfaces were covered with 2.5 grams of vehicle containing 0.63 mg of recombinant tissue plasminogen activator. The five control rabbits received the same amount of vehicle containing no recombinant tissue plasminogen activator. The rabbits were sutured closed in two layers and reopened after 7 days. The results of the extent of the elimination of existing adhesions and reformation of postoperative adhesions (FIG. 2) indicate that a thrombolytic or fibrinolytic agent, such as recombinant tissue plasminogen activator, in the novel composition of this invention and applied to the site of prior adhesion formation such that there is continuous release of the agent is as effective in eliminating and preventing the reformation of adhesions after surgical lysis as it is in preventing initial adhesion formation.

High doses of recombinant tissue plasminogen activator administered as a thrombolytic or fibrinolytic agent have been shown to cause moderate decreases in systemic fibrinogen (Rao, A. K. et al., Clin. Res. 34, 337A [1986]). Whether the use of recombinant tissue plasminogen activator in gel in the prevention of adhesion formation contributed to systemic fibrinogen degradation was assessed by assaying blood samples from four rabbits using the recombinant tissue plasminogen activator inhibitor, D-Phe-Pro-Arg-chloromethylketone (Mohler, M. A. et al., Thromb. Heam. 56:2 [1986]) at 0, 2, 3, 4 and 24 hours after the application of 2.5 grams of vehicle containing 0.63 mg of recombinant tissue plasminogen activator in the peritoneal cavity. Plasma samples were assayed for recombinant tissue plasminogen activator by a specific ELISA with a sensitivity of 15 ng recombinant tissue plasminogen activator per ml of plasma. There was no evidence of circulating recombinant tissue plasminogen activator at any time. Since recombinant tissue plasminogen activator is rapidly cleared by the liver, the same plasma samples were measured for changes in fibrinogen by a thrombin dependent method; no decreases in circulating fibrinogen were evident indicating that the recombinant tissue plasminogen activator is not readily adsorbed into the circulation from the peritoneal cavity at a rate which would elicit changes in the coagulation system in rabbits.

Buckman, R. F. et al., J. Surg. Res. 20:1 (1976) have suggested that persistent depression of plasminogen activator activity resulting from trauma with consequent ischemic damage to the peritoneal surface, is a major stimulus to adhesion formation. Conversely, a maintenance of intrinsic fibrinolytic system may lead to the resolution of fibrin and permanent adhesion may not develop. Although the time course of depressed plasminogen activator activity is not known in the pathogenesis of fibrous adhesion formation, a single intraperitoneal postoperative dose of a soluble fibrinolytic agent as discussed above is not sufficient. This invention established for the first time that a sparingly soluble form of a thrombolytic agent such as recombinant tissue plasminogen activator formulated applied directly to the site of potential adhesion formation supplements the depressed endogenous fibrinolytic system to prevent adhesion formation, most likely by a prolonged slow continuous release of the enzyme.

Possible complications from the intraperitoneal use of recombinant tissue plasminogen activator such as systemic fibrinogenolysis and wound healing were not observed. Intraperitoneal bleeding was not encountered in these animal studies.

TABLE 2

| Rabbit Identification Treatment Method | 1 | 2 | 3 | 4 | 5 | 6 |
|---|---|---|---|---|---|---|
| FORMULATION 1: | | | Grade | | | |
| Control | 4 | 3 | 0 | 4 | 4 | 3 |
| Treated | 0 | 3 | 3 | 0 | 5 | 0 |
| FORMULATION 2: | | | | | | |
| Control | 5 | 4 | 4 | 1 | 0 | 0 |
| Treated | 0 | 0 | 0 | 0 | 0 | 4 |
| FORMULATION 3: | | | | | | |
| Control | 4 | 4 | 4 | 4 | 4 | 4 |
| Treated | 3 | 3 | 5 | 5 | 5 | |
| FORMULATION 4: | | | | | | |
| Control | 4 | 4 | 4 | 4 | 4 | 4 |
| Treated | 0 | 1 | 0 | 3 | 0 | 0 |
| FORMULATION 5: | | | | | | |
| Control | 4 | 4 | 4 | 4 | 5 | 5 |
| Treated | 0 | 0 | 0 | 0 | 0 | 3 |
| FORMULATION 6: | | | | | | |
| Control | 2 | 2 | 3 | 5 | 5 | 5 |
| Treated | 0 | 0 | 0 | 0 | 0 | 1 |
| FORMULATION 7: | | | | | | |
| Control | 1 | 4 | 4 | 4 | 5 | 5 |
| Treated | 0 | 0 | 0 | 0 | 0 | 3 |
| FORMULATION 8: | | | | | | |
| Control | 0 | 4 | 4 | 4 | 5 | 5 |
| Treated | 0 | 0 | 0 | 0 | 0 | 0 |
| FORMULATION 9: | | | | | | |
| Control | 4 | 5 | 5 | 5 | 4 | 3 |
| Treated | 0 | 0 | 0 | 0 | 0 | 0 |

TABLE 3

|  | No Adhesion | Blunt Dissection | Sharp Dissection | Sharp Dissection (with difficulty) |
|---|---|---|---|---|
| Vehicle only | 0 | 3 | 2 | 1 |
| Vehicle + 0.16 mg of recombinant tissue plasminogen activator | 0 | 3 | 1 | 2 |
| Vehicle + 0.31 mg of recombinant tissue plasminogen activator | 4 | 2 | 0 | 0 |
| Vehicle + 0.63 mg of recombinant tissue plasminogen activator | 5 | 1 | 0 | 0 |

The severity of the adhesions which formed in the dose response study (FIG. 1) were scored with respect to the surgical effort required to separate the adhered tissues. The number of animals with adhesions requiring surgical lysis is shown.

EXAMPLE 3

Sparingly Soluble Composition Effect on Pelvic Adhesions

Female New Zealand white rabbits (approx. 3.0 kg) were anesthetized with ketamine, Rompun and Accepromazine and laparotomies were performed. The entire surface of the uterine horns was exposed and abraded until punctate bleeding occurred followed by severe tissue damage to the horns with electrocautery. Tissue plasminogen activator in the novel composition of this invention was delivered to the traumatized uterine horns as a gel formulation (Amogel— see Formulation 5 described above). After replacement of the uterine horns into the pelvic cavity, the muscle layer of the abdomen was sutured closed and the skin layer was closed with surgical staples. After fourteen days, the rabbits were anesthetized as described above and repeat laparotomies were performed to determine the extent of adhesions formed. The extent of adhesions were determined by quantitation of the surface area of the uterine horns which was adherent to itself.

|  | no gel | gel only | 2.5 gr of novel composition | | |
|---|---|---|---|---|---|
|  |  |  | 0.125 mg/gr* | 0.25 mg/g** | 0.6 mg/g** |
| % adherent tissue | 53% ± 32 | 35.6% ± 20 | 31.67% ± 22.1 | 25% ± 16.3 | 18.9% ± 11.3 |

*mg/gr - mg of tissue plasminogen activator/gram of gel
**$p<0.05$ as determined as determined by students t-test as compared to no gel group.

Animals having adhesions that were surgically amenable to lysis of the adhesions were then grouped such that the mean % adherent tissue was approximately 25%. After their adhesions were separated, novel compositions containing tissue plasminogen activator were applied in a similar manner as described above. After fourteen days, the rabbits were euthanized and the percent adherent tissue scored upon macroscopic examination of the uterine horns.

|  | gel only | 2.5 gr of novel composition | | |
|---|---|---|---|---|
|  |  | 1 mg/gr* | 5 mg/gr* | 10 mg/gr* |
| % re-adherent tissue | 61.86 | 37.36 | 20 | 7.5 |
| Δ change from extent of initial adhesion to reformation of adhesions | 40.63% ± 12.9 | 11.11% ± 22.5 | 0% ± 13.2 | −12.5% ± 0 |

*mg/gr - mg of tissue plasminogen activator/gram of gel

EXAMPLE 4

Sparingly Soluble Composition Effect on Ophthalmic Adhesions

A complication of cataract surgery is adhesion formation leading to strabismus surgery. Prevention of adhesion formation consequent to ophthalmic surgery has been attempted using hyaluronic acid. Hyaluronic acid is a natural carbohydrate consisting of alternating β-D-Glucuronic acid and 2-acetamido-2-deoxy-β-D-glucose. The use of hyaluronic acid, or a chemically modified form of this compound in reducing post-surgical adhesion in eye surgery and in tendon repair operations have been reported. (Searl, S. S., Meta, H. S. and Lindahi, K. J., Ann. Ophthalmol. 19(7):259, [1987]; Weiss, C., Levy, H., Denlinger, J., Suros, J. and Weiss, H., Bull. Hosp. Jt. Dis. Orhtop. Inst. 46:9–15 [1986]; Weiss, C. Suros, J., Michalow, A., Denlinger, J., Moore, M., Tejeiro, W., Bull Hosp. Jt. Dis. Orthop. Inst. 47:31–39 [1987]). The efficacy of these substances in preventing adhesion has not been conclusively demonstrated in these studies.

However, due to its biocompatibility, hyaluronic acid solutions could be used to deliver a sparingly soluble enzyme, such as t-PA. The following formulation is an example of the novel composition of this invention comprising a sparingly soluble enzyme, such as tissue plaminogen activator suspended in a bioerodable, mucilaginous carrier, such as hyaluronic acid.

Formulation

| t-PA | 0.1 to 1 mg |
|---|---|
| Hyaluronic acid | 3 to 50 mg |
| NaOH to adjust pH to between | 4.5 to 8.0 |
| WFI QS | 1 mL |

The hyaluronic acid is dissolved in sterile water while titrating the solution to the desired pH (preferably 5.0 to 6.0) with NaOH, and adding homogeneously dispersed t-PA powder. The composition is stirred until a mucilaginous gel is formed. The mucilaginous t-PA formulation of this invention is applied immediately following cataract surgery or sirabisimus surgery to the site of potential fibrin deposition or adhesion formation.

EXAMPLE 5

Sparingly Soluble Composition Effect On Fibrin Deposition

Fibrin deposition typically occurs at the site of intraabdominal infection, providing an insular compartment for bacterial proliferation. This compartmentalization, while isolating the infection, also isolates the infection from host defense mechanisms. A similar problem of bacterial peritonitis has been observed in patients receiving continuous ambulatory peritoneal dialysis (CAPD). (Norris, K. D. et al., Am. J. of Kidney Disease, 10(1):62–65 [1987]). Sequestration of bacteria within fibrin clots in CAPD is thought to serve as a nidus for bacteria, protecting them from being killed by antibiotics and leukocytes. Heparin and streptokinase in solution have been administered to these CAPD patients.

A fibrin clot peritonitis model has been developed to inoculate rats intraperitoneally with infected clots. (Wells, C. L., et al., J. Antimicrob. Chemoth. 15(Suppl: C):199–206 [1985]). The novel composition of this invention is applied following surgery at or near the site of potential fibrin deposition and abscess formation. Laparotomy is performed and the peritoneal cavity is inspected for abscess formation.

We claim:

1. The method of treating an animal to prevent fibrin deposition or adhesion formation or reformation comprising administration of a composition to a site of potential fibrin or adhesion formation consequent to the animal undergoing surgery wherein the composition comprises a therapeutically effective amount of a sparingly soluble form of tissue plasminogen activator as a precipitated solid molecular form that is continuously released at that site for a period of time of about three days to two weeks.

2. The method of claim 1 wherein the composition includes an inert adherence enhancing vehicle.

3. The method of claim 2 wherein the therapeutically effective amount of a sparingly soluble form of tissue plasminogen activator is in the range of about from 0.20 mg/gm of inert adherence enhancing vehicle to about 2.5 mg/gm of inert adherence enhancing vehicle.

4. The method of claim 2 wherein the therapeutically effective amount of a sparingly soluble form of tissue plasminogen activator is in the range of about from 0.25 mg/gm of inert adherence enhancing vehicle to about 1.0 mg/gm of inert adherence enhancing vehicle.

5. The method of claim 2 wherein the inert adherence enhancing vehicle is a water soluble gel.

6. The method of claim 2 wherein the inert adherence enhancing vehicle is a semisolid vehicle.

7. The method of claim 6 wherein the semisolid vehicle is petrolatum jelly.

8. The method of claim 2 wherein the vehicle is a bioerodable polymer.

9. The method of claim 2, wherein the vehicle is hyaluronic acid.

10. The method of claim 1 wherein the fibrin deposition is consequent to the animal having peritonitis.

* * * * *